(12) United States Patent
Barrett

(10) Patent No.: US 6,380,465 B1
(45) Date of Patent: Apr. 30, 2002

(54) CYTOCHROME P450 ENZYMES AND RELATED COMPOUNDS AND METHODS

(75) Inventor: Michael Barrett, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/351,229

(22) Filed: Jul. 11, 1999

Related U.S. Application Data

(60) Provisional application No. 60/092,596, filed on Jul. 12, 1998.

(51) Int. Cl.⁷ ........................ C12N 15/09; C12N 15/29; C12N 15/82; A01H 5/00
(52) U.S. Cl. .................... 800/300; 800/300.1; 800/302; 800/312; 800/317; 800/317.1; 800/317.3; 800/320; 800/320.3; 800/322; 800/309; 800/323; 800/323.3; 435/69.1; 435/419; 435/483; 435/468; 435/320.1; 536/23.1; 536/23.2; 536/23.6
(58) Field of Search ............................... 800/300, 300.1, 800/302, 312, 317.3, 320.3, 320, 322, 317, 317.1, 309, 323, 323.3; 435/69.1, 320.1, 483, 468, 418, 419; 536/23.1, 23.2, 23.6

(56) References Cited

U.S. PATENT DOCUMENTS 5,212,296 A * 5/1993 Dean et al. ................. 536/23.2
5,734,086 A * 3/1998 Scott et al. .................. 800/205

OTHER PUBLICATIONS

Frey et al. Mol. Gen. Genet. vol. 246, pp. 100–109, 1995.*
Mangold et al. Plant Science, vol. 96, pp. 129–136, 1994.*
Pierrel, et al, 224 *Eur J Biochem* 835 (1994). Presentation, *Weed Sci Soc of Amer* (Feb. 1997).
http://drnelson.utmem.edu/biblioD.html#72A Ph.D. Dissertation of Laura Boldt (Apr. 15, 1992).
Baerg, et al, 55 *Pesticide Biochemistry and Physiology* 10 (1996) Ph.D. Dissertation of Roger J. Baerg (Nov. 4, 1994).

* cited by examiner

*Primary Examiner*—Gary Benzion
*Assistant Examiner*—Medina A. Ibrahim
(74) *Attorney, Agent, or Firm*—McDermott, Will & Emery

(57) ABSTRACT

The present invention provides, inter alia, nucleic acids which encode P450s in corn that, when expressed in the presence of a reductase, metabolize compounds exemplary of several distinct classes of insecticides and herbicides. The invention also includes amino acids encoded by the nucleic acids, as well as vectors, cells and eukaryotes comprising the nucleic or amino acid compounds. Also included are methods using the materials provided.

14 Claims, 11 Drawing Sheets

```
                                                        SEQ ID NO: 1
CCGTATCCGTCCTCTGCTTCTCTCTTCCATTGCCCCAAGCCGCCACCAATGGCGACCTGC     60
                                                         M  A  T  C      4
                                                        SEQ ID NO: 2
GATCTGCTGATGCTGCGGGAAGCATCTCCGTGGGCGCTGGCCGGCGCGGTGGCGTCCGTG    120
 D  L  L  M  L  R  E  A  S  P  W  A  L  A  G  A  V  A  S  V     24
TCGCTGTTGTGGCTGGTGGCCTGGACGCTGGAGTGGGCCTGGTGGACACCTTGGCGGCTC    180
 S  L  L  W  L  V  A  W  T  L  E  W  A  W  W  T  P  W  R  L     44
GATCGGGCCCTGCGGGCCCAGGGCCTCAATGGCACCAGGTACCGCCTCTTCACCGGCGAC    240
 D  R  A  L  R  A  Q  G  L  N  G  T  R  Y  R  L  F  T  G  D     64
CTGAGGGAAACCGCCCGGGTTAACCGGGAGGCTCGCAAGAAGCCGCTGCCGCTCGGCTGC    300
 L  R  E  T  A  R  V  N  R  E  A  R  K  K  P  L  P  L  G  C     84
CACGACATCACCCCACGCGTGCAGCCCATGCATCACAGCACCATCAAGGAATACGGGAAA    360
 H  D  I  T  P  R  V  Q  P  M  H  H  S  T  I  K  E  Y  G  K    104
CTATCGTTCACCTGGTTCGGCCCAACACCAAGGGTGATGATTCCTGACCCAGAGTTAGTC    420
 L  S  F  T  W  F  G  P  T  P  R  V  M  I  P  D  P  E  L  V    124
AAAGAGGTGCTGTCTAATAAGTTTGGCCACTTTGGCAAACCAAGGAGTAGCCGCATTGGG    480
 K  E  V  L  S  N  K  F  G  H  F  G  K  P  R  S  S  R  I  G    144
AGGTTGCTAGCCAACGGGCTTGTAAATCATGATGGTGAAAAATGGGCAAAGCACAGGAGA    540
 R  L  L  A  N  G  L  V  N  H  D  G  E  K  W  A  K  H  R  R    164
ATTCTTAATCCTGCATTTCACCATGAAAAAATAAAGGGGATGATGCCAGTATTTTCTACC    600
 I  L  N  P  A  F  H  H  E  K  I  K  G  M  M  P  V  F  S  T    184
TGCTGTATTGAAATGATTACTAGATGGGATAATTCAATGTCTTCCGAGGGATCTTCTGAG    660
 C  C  I  E  M  I  T  R  W  D  N  S  M  S  S  E  G  S  S  E    204
ATAGATGTCTGGCCTGAGTTCCAGAATCTTACTGGAGATGTTATCTCAAGAACTGCGTTT    720
 I  D  V  W  P  E  F  Q  N  L  T  G  D  V  I  S  R  T  A  F    224
GGGAGCAACTATCAAGAAGGGAGGAGAATTTTTGAGCTACAAGGAGAACTAGCTGAACGC    780
 G  S  N  Y  Q  E  G  R  R  I  F  E  L  Q  G  E  L  A  E  R    244
CTCATCCAATCTGTTCAGACAATATTTATCCCAGGCTATTGGTTCTTGCCCACCAAAAAC    840
 L  I  Q  S  V  Q  T  I  F  I  P  G  Y  W  F  L  P  T  K  N    264
AACAGAAGGATGAGAGCAATCGATGTAGAGATCCGCAAAATTCTCCGTGAAATAATTGGG    900
 N  R  R  M  R  A  I  D  V  E  I  R  K  I  L  R  E  I  I  G    284
AAGAGAGAGAAGGATACTAAAAACAGAGAAACAAATAAAGATGACTTGCTGGGCTTATTA    960
 K  R  E  K  D  T  K  N  R  E  T  N  K  D  D  L  L  G  L  L    304
CTGGAGTCAAACACAAGGCAATCAAATGGAAATGCAAGCCTGGGATTGACAACAGAAGAT   1020
 L  E  S  N  T  R  Q  S  N  G  N  A  S  L  G  L  T  T  E  D    324
GTGATTGAGGAATGCAAGTTATTTTACTTTGCAGGTATGGAGACAACATCAGTCCTGCTT   1080
 V  I  E  E  C  K  L  F  Y  F  A  G  M  E  T  T  S  V  L  L    344
ACTTGGACACTTATTGTGCTAAGCATGCACCCAGAATGGCAAGAGAGAGCAAGAGAAGAG   1140
 T  W  T  L  I  V  L  S  M  H  P  E  W  Q  E  R  A  R  E  E    364
GTTTTGAGCCACTTTGGAAGAACCACACCAGATTATGATAGCTTGAGCCGCCTCAAGACT   1200
 V  L  S  H  F  G  R  T  T  P  D  Y  D  S  L  S  R  L  K  T    384
GTAACCATGATTCTACATGAGGTCCTTAGGTTGTACCCACCGGCAACCTTTCTAACCAGA   1260
 V  T  M  I  L  H  E  V  L  R  L  Y  P  P  A  T  F  L  T  R    404
AGAACTTATAAGGAAATGGAGCTCGGTGGAATCAAATATCCTGCAGGAGTGGAGCTCCTT   1320
 R  T  Y  K  E  M  E  L  G  G  I  K  Y  P  A  G  V  E  L  L    424
CTGCCCGTCATCTTCATTCACCATGATCCCGACATTTGGGGAAAAGACGCAAGCGAGTTC   1380
 L  P  V  I  F  I  H  H  D  P  D  I  W  G  K  D  A  S  E  F    444
AACCCAGAAAGGTTTGCCAACGGCATCTCCAGCGCAACCAGGCATCAGGCTGCTTTCTTT   1440
 N  P  E  R  F  A  N  G  I  S  S  A  T  R  H  Q  A  A  F  F    464
CCGTTCGGAGGGGGCCCCAGGATCTGCATCGGCCAGAGCTTTGCGTTGCTGGAAGCCAAG   1500
 P  F  G  G  G  P  R  I  C  I  G  Q  S  F  A  L  L  E  A  K    484
ATGACGCTATGCACCATCCTCCAGCGCTTCTCGTTCGAGCTCTCACCATCCTACACCCAC   1560
 M  T  L  C  T  I  L  Q  R  F  S  F  E  L  S  P  S  Y  T  H    504
GCGCCGTACACCGTGATAACACTGCACCCTCAGCACGGTGCTCAGATAAGGCTCAAAAAG   1620
 A  P  Y  T  V  I  T  L  H  P  Q  H  G  A  Q  I  R  L  K  K    524
CTTTCTCCGTGATGCTCCTTCGATGCTGCTACCGGACACTACTTTCGTTACTGACCGCGT   1680
 L  S  P  *                                                     528
ATGTAGAAAAATATTTCTTATTTAGTATGTATTTTAGGATATAAATAAAAAGAGGGCGC   1740
ATATTAATGGGAAATAAGTTCCCTTGTATGCATTGCGATGTAATTTTGGGAAGATTTGGC   1800
AAGGAACTTAATTATACAATATATGTATTGTTTTTAAGTTTAAAAAAAAAAAAAAAAAAA   1860
AAAAAAAAAAAAAAAAAAAAAAAA 1884
```

FIG. 1

```
GCACGAGGCCGCGTTCCTCGGCATTGCCCTTTGCGCAGCGGCAGCGCTCTTCCTTTTGCG    60
  H  E  A  A  F  L  G  I  A  L  C  A  A  A  A  L  F  L  L  R    20
TGGCCGGCGCCCGGTCTACAACCCCCCGCCGGGCCCCAAGCCATGGCCGATCATCGGCAA   120
  G  R  R  P  V  Y  N  P  P  P  G  P  K  P  W  P  I  I  G  N    40
CCTTAACCTCATGGGCGAGCTGCCCCACCGCTCCATGAACGAGCTCTCCAAGCGGTACGG   180
  L  N  L  M  G  E  L  P  H  R  S  M  N  E  L  S  K  R  Y  G    60
TCCGCTCATGCAGCTCTGGTTCGGGTCGTTGCCTGTTGTCGTCGGCGCGTCCGCCGAGAT   240
  P  L  M  Q  L  W  F  G  S  L  P  V  V  V  G  A  S  A  E  M    80
GGCAAAGCTCTTCCTCAAGACCAACGACGCGGCGTTCTCCGACCGGCCGAGGTTCGCAGT   300
  A  K  L  F  L  K  T  N  D  A  A  F  S  D  R  P  R  F  A  V   100
CGGCAAGTACACCGCGTACGACTGCTCCGGCCTTCTGTGGGCTCCTTTTGAGCCGTACCT   360
  G  K  Y  T  A  Y  D  C  S  G  L  L  W  A  P  F  E  P  Y  L   120
GCGCCAGGCACGCAGGATCTGCGCCACCGAGCTCTTCAGCGCCACGCGGCTCGAGTCCTT   420
  R  Q  A  R  R  I  C  A  T  E  L  F  S  A  T  R  L  E  S  F   140
CGAGCACATCCGCGACGAGGAGGTGCGCGTGATGCTCCGACAGCTGCGCCAAGCGGCTGG   480
  E  H  I  R  D  E  E  V  R  V  M  L  R  Q  L  R  Q  A  A  G   160
GCGCACCGTGCGGCTTAGGGACTACCTGCAGATGTTGGCGCTCGGCGTGATCTCGCGCAT   540
  R  T  V  R  L  R  D  Y  L  Q  M  L  A  L  G  V  I  S  R  I   180
AGTTCTGGGCAAGAAGTACGTCATGGAGGAGGCGGCGGACGGTGAGGGGGACTCAGCGCC   600
  V  L  G  K  K  Y  V  M  E  E  A  A  D  G  E  G  D  S  A  P   200
GGCGATAACGCCTGCCGAGTTCAGGGAGATGGTGGACGAGTTCTTCGCGCTTCACGGTGC   660
  A  I  T  P  A  E  F  R  E  M  V  D  E  F  F  A  L  H  G  A   220
GTTTAACATTGGTGATTATATCCCTTGGCTAGATTGGCTGGACCTGCAGGGCTACGTTGC   720
  F  N  I  G  D  Y  I  P  W  L  D  W  L  D  L  Q  G  Y  V  A   240
TAGGATGAAGAGAATGAAGGCGAGGTTTGGTCGATTCCTGGAACGAGTCTTGGACGTGCA   780
  R  M  K  R  M  K  A  R  F  G  R  F  L  E  R  V  L  D  V  H   260
CAACGAGCGGCGACTACGCGAGGGAGGGAACTTTGTGGCAAAGGATATGTTGGACGTGCT   840
  N  E  R  R  L  R  E  G  G  N  F  V  A  K  D  M  L  D  V  L   280
GCTGCAGCTGGCCGATGACACTAGTCTTGAAGTCCAGCTCAGCAGGGACAATGTTAAGGC   900
  L  Q  L  A  D  D  T  S  L  E  V  Q  L  S  R  D  N  V  K  A   300
TATCACACAGGACCTAATCATCGCAGGCACGGATAGTAATGCAAACACGCTGGAGTGGGC   960
  I  T  Q  D  L  I  I  A  G  T  D  S  N  A  N  T  L  E  W  A   320
TGTCTCGGAGCTCCTCAAGAACCCTAAGATCTTAGCCAAGGCCATGGAGGAGCTGAACCA  1020
  V  S  E  L  L  K  N  P  K  I  L  A  K  A  M  E  E  L  N  H   340
TGTCATAAGGCCGGACCGACTGGTGACGGAAAGCGACCTCCCTCGCCTCCCCTACATCGA  1080
  V  I  R  P  D  R  L  V  T  E  S  D  L  P  R  L  P  Y  I  E   360
GGCTGTGCTCAAGGAGACCATGCGCGTGCACCCTGCCGCGCCGATGCTGGCACCCCACGT  1140
  A  V  L  K  E  T  M  R  V  H  P  A  A  P  M  L  A  P  H  V   380
GGCCCGCGAGGACACATCCGTGGACGGATACGACGTGCTCGCTGGCACGGTCTTGTTCAT  1200
  A  R  E  D  T  S  V  D  G  Y  D  V  L  A  G  T  V  L  F  I   400
CAACGTGTGGGCAATCGGCCGCGACCCTGGACTGTGGGACGCGCCGGAGGAGTTCCGGCC  1260
  N  V  W  A  I  G  R  D  P  G  L  W  D  A  P  E  E  F  R  P   420
GGAGCGGTTCGTCGAGAGCAAGATCGACGTGAGGGGCCATGACTTCCAGCTGCTGCCGTT  1320
  E  R  F  V  E  S  K  I  D  V  R  G  H  D  F  Q  L  L  P  F   440
CGGCTCTGGCCGGCGAATGTGCCCCGGGATCAACCTCGCGCTAAAGGTGATGGCTTTGAG  1380
  G  S  G  R  R  M  C  P  G  I  N  L  A  L  K  V  M  A  L  S   460
TCTTGCCAATCTGCTACACGGCTTCGAGTGGAGGCTTCCGGACGGCGTGACGGCAGAGGA  1440
  L  A  N  L  L  H  G  F  E  W  R  L  P  D  G  V  T  A  E  E   480
GCTGAGCATGGATGAGGCCTTCAAGCTCGCGGTACCGCGTAAATTCCCGCTCATGGTCGT  1500
  L  S  M  D  E  A  F  K  L  A  V  P  R  K  F  P  L  M  V  V   500
GGCCGAGCCCAGGTTGCCAGCTCGCCTGTATACTGGCGCTTGATGCCAGTACGTGTCTTC  1560
  A  E  P  R  L  P  A  R  L  Y  T  G  A  *                     514
GGTTGTTGGCATGCGTGGAGTATAGCACATGATTTTCAGCTCTTGGAACTTTGTTTTAAT  1620
AAAACACAAATATATGTGTTATGTTGGTTAGATGAATGTGAATATAAAGTTGACAACCTA  1680
GGTAATTCGAACCCCTATTGGTATATAATTTTACTTTATTTTTGCATAACTGTGTAAACT  1740
GGTGGTCATGGACGTTGAAGTTAATATTTGGACTGTGGATTAGATTAAAAAAAAAAAAAA  1800
AAAAAA                                                        1806
```

FIG. 2

SPECTRA DEMONSTRATING (PEAK AT 450)
EXPRESSION OF 72A1 IN YEAST MICROSOMES

| For CYP72A1 | | | |
|---|---|---|---|
| Gene | Nucleotide Identity | Protein Identity | Protein Similarity |
| CYP72C from Catharanthus | 55.0% | 49.1% | 61.5% |
| CYP72A1 from Catharanthus | 53.2% | 48.2% | 60.3% |
| CYP72B from Catharanthus | 49.6% | 48.6% | 60.7% |
| CYP72A from Nicotiana | 52.8% | 44.4% | 54.0% |
| For CYP92A1 | | | |
| CYP92A2 from Nicotiana | 59.0% | 58.2% | 65.6% |
| CYP92A3 from Nicotiana | 56.5% | 57.6% | 64.5% |
| CYP98A1 from Sorghum | 51.2% | 36.4% | 47.3% |
| CYP98A2 from Soybean | 49.0% | 38.6% | 48.8% |
| CYP71C2 from Maize | 51.7% | 32.8% | 43.9% |

FIG. 4

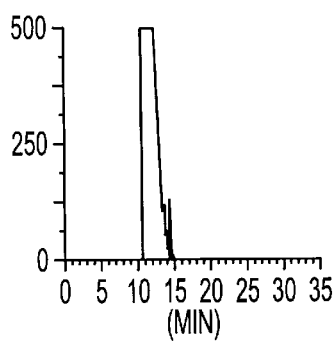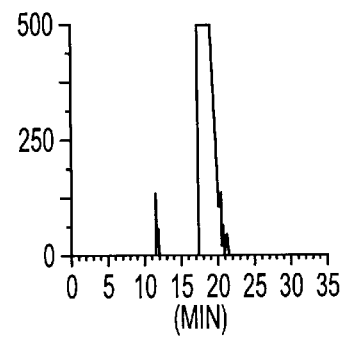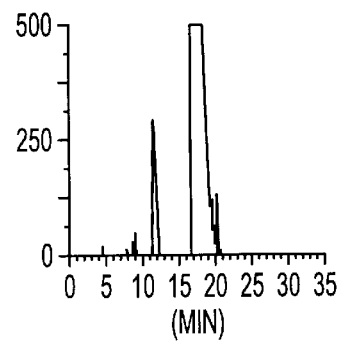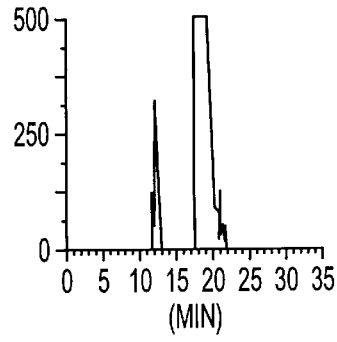
FIG. 8

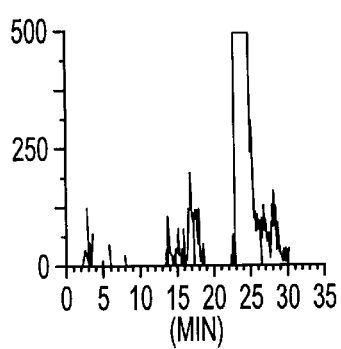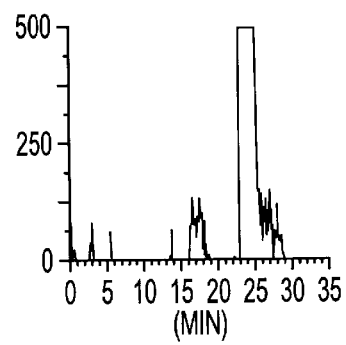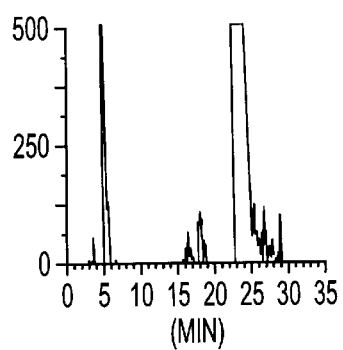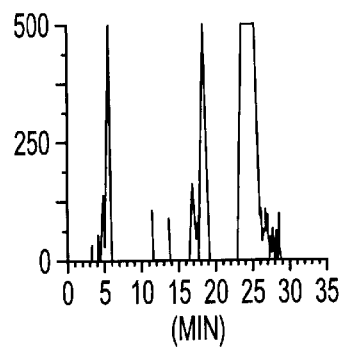
FIG. 9

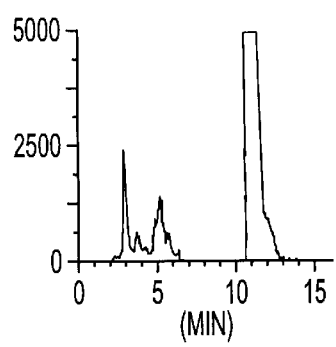
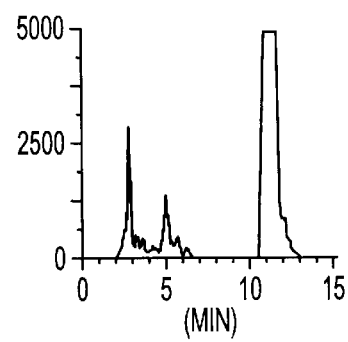
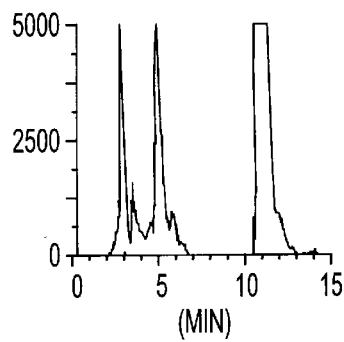
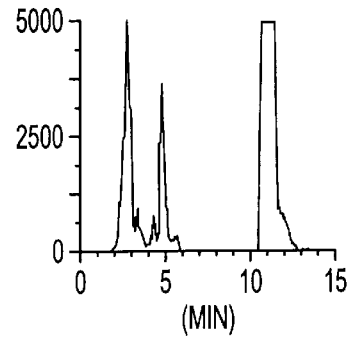
FIG. 10

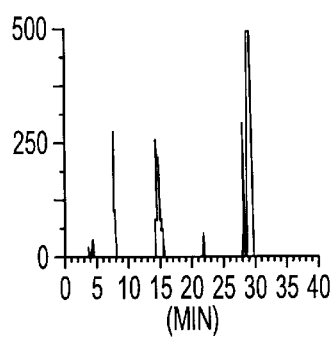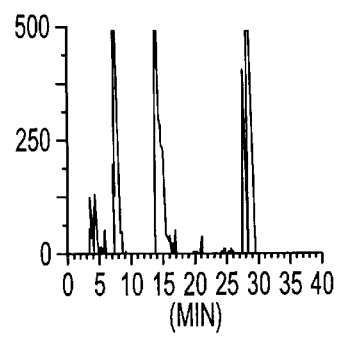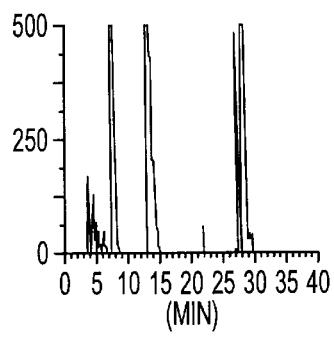
FIG. 11

SEQUENCE LISTING

<160> NUMBER OF SEQ ID NOS: 4

<210> SEQ ID NO 1
<211> LENGTH: 1584
<212> TYPE: DNA
<213> ORGANISM: Zea mays

<400> SEQUENCE: 1

```
atggcgacct gcgatctgct gatgctgcgg gaagcatctc cgtgggcgct ggccggcgcg      60
gtggcgtccg tgtcgctgtt gtggctggtg gcctggacgc tggagtgggc ctggtggaca     120
ccttggcggc tcgatcgggc cctgcgggcc cagggcctca atggcaccag gtaccgcctc     180
ttcaccggcg acctgaggga aaccgcccgg gttaaccggg aggctcgcaa gaagccgctg     240
ccgctcggct gccacgacat caccccacgc gtgcagccca tgcatcacag caccatcaag     300
gaatacggga aactatcgtt cacctggttc ggcccaacac caagggtgat gattcctgac     360
ccagagttag tcaaagaggt gctgtctaat aagtttggcc actttggcaa accaaggagt     420
agccgcattg ggaggttgct agccaacggg cttgtaaatc atgatggtga aaaatgggca     480
aagcacagga gaattcttaa tcctgcattt caccatgaaa aaataaaggg gatgatgcca     540
gtattttcta cctgctgtat tgaaatgatt actagatggg ataattcaat gtcttccgag     600
ggatcttctg agatagatgt ctggcctgag ttccagaatc ttactggaga tgttatctca     660
agaactgcgt ttgggagcaa ctatcaagaa gggaggagaa tttttgagct acaaggagaa     720
ctagctgaac gcctcatcca atctgttcag acaatattta tcccaggcta ttggttcttg     780
cccaccaaaa acaacagaag gatgagagca atcgatgtag agatccgcaa aattctccgt     840
gaaataattg ggaagagaga gaaggatact aaaaacagag aaacaaataa agatgacttg     900
ctgggcttat tactggagtc aaaacacaag caatcaaatg gaaatgcaag cctgggattg     960
acaacagaag atgtgattga ggaatgcaag ttattttact ttgcaggtat ggagacaaca    1020
tcagtcctgc ttacttggac acttattgtg ctaagcatgc acccagaatg gcaagagaga    1080
gcaagagaag aggttttgag ccactttgga agaaccacac cagattatga tagcttgagc    1140
cgcctcaaga ctgtaaccat gattctacat gaggtcctta ggttgtaccc accggcaacc    1200
tttctaacca gaagaactta taggaaatg gagctcggtg aatcaaata tcctgcagga    1260 gtggagctcc ttctgcccgt catcttcatt caccatgatc ccgacatttg ggaaaagac    1320 gcaagcgagt tcaacccaga aaggtttgcc aacggcatct ccagcgcaac caggcatcag    1380
gctgctttct ttccgttcgg agggggcccc aggatctgca tcggccagag ctttgcgttg    1440
ctggaagcca agatgacgct atgcaccatc ctccagcgct tctcgttcga gctctcacca    1500
tcctacaccc acgcgccgta caccgtgata acactgcacc ctcagcacgg tgctcagata    1560
```

```
aggctcaaaa agctttctcc gtga                                           1584
```

<210> SEQ ID NO 2
<211> LENGTH: 199
<212> TYPE: PRT
<213> ORGANISM: Zea mays

<400> SEQUENCE: 2

```
Met Ala Thr Cys Asp Leu Leu Met Leu Arg Glu Ala Ser Pro Trp Ala
 1               5                  10                  15

Leu Ala Gly Ala Val Ala Ser Val Ser Leu Leu Trp Leu Val Ala Trp
            20                  25                  30

Thr Leu Glu Trp Ala Trp Trp Thr Pro Trp Arg Leu Asp Arg Ala Leu
        35                  40                  45

Arg Ala Gln Gly Leu Asn Gly Thr Arg Tyr Arg Leu Phe Thr Gly Asp
    50                  55                  60

Leu Arg Glu Thr Ala Arg Val Asn Arg Glu Ala Arg Lys Lys Pro Leu
65                  70                  75                  80

Pro Leu Gly Cys His Asp Ile Thr Pro Arg Val Gln Pro Met His His
                85                  90                  95

Ser Thr Ile Lys Glu Tyr Gly Lys Leu Ser Phe Thr Trp Phe Gly Pro
            100                 105                 110

Thr Pro Arg Val Met Ile Pro Asp Pro Glu Leu Val Lys Glu Val Leu
        115                 120                 125

Ser Asn Lys Phe Gly His Phe Gly Lys Pro Arg Ser Ser Arg Ile Gly
    130                 135                 140

Arg Leu Leu Ala Asn Gly Leu Val Asn His Asp Gly Glu Lys Trp Ala
145                 150                 155                 160

Lys His Arg Arg Ile Leu Asn Pro Ala Phe His His Glu Lys Ile Lys
                165                 170                 175

Gly Met Met Pro Val Phe Ser Thr Cys Cys Ile Glu Met Ile Thr Arg
            180                 185                 190

Trp Asp Asn Ser Met Ser Ser
        195
```

<210> SEQ ID NO 3
<211> LENGTH: 1806
<212> TYPE: DNA
<213> ORGANISM: Zea mays

<400> SEQUENCE: 3

```
gcacgaggcc gcgttcctcg gcattgccct ttgcgcagcg gcagcgctct tccttttgcg     60
tggccggcgc ccggtctaca accccccgcc gggccccaag ccatggccga tcatcggcaa    120
ccttaacctc atgggcgagc tgccccaccg ctccatgaac gagctctcca agcggtacgg    180
tccgctcatg cagctctggt tcgggtcgtt gcctgttgtc gtcggcgcgt ccgccgagat    240
ggcaaagctc ttcctcaaga ccaacgacgc ggcgttctcc gaccggccga ggttcgcagt    300
cggcaagtac accgcgtacg actgctccgg ccttctgtgg gctccttttg agccgtacct    360
gcgccaggca cgcaggatct gcgccaccga gctcttcagc gccacgcggc tcgagtcctt    420
cgagcacatc cgcgacgagg aggtgcgcgt gatgctccga cagctgcgcc aagcggctgg    480
gcgcaccgtg cggcttaggg actacctgca gatgttggcg ctcggcgtga tctcgcgcat    540
agttctgggc aagaagtacg tcatggagga ggcggcggac ggtgagggg actcagcgcc    600
ggcgataacg cctgccgagt tcagggagat ggtggacgag ttcttcgcgc ttcacggtgc    660
```

-continued

```
gtttaacatt ggtgattata tcccttggct agattggctg gacctgcagg gctacgttgc    720
taggatgaag agaatgaagg cgaggtttgg tcgattcctg aacgagtct tggacgtgca     780
caacgagcgg cgactacgcg agggagggaa ctttgtggca aaggatatgt tggacgtgct    840
gctgcagctg ccgatgaca ctagtcttga agtccagctc agcagggaca atgttaaggc     900
tatcacacag gacctaatca tcgcaggcac ggatagtaat gcaaacacgc tggagtgggc    960
tgtctcggag ctcctcaaga accctaagat cttagccaag gccatggagg agctgaacca   1020
tgtcataagg ccggaccgac tggtgacgga aagcgactcc ctcgcctccc ctacatcgag   1080
gctgtgctca aggagaccat gcgcgtgcac cctgccgcgc cgatgctggc accccacgtg   1140
gcccgcgagg acacatccgt ggacggatac gacgtgctcg ctggcacggt cttgttcatc   1200
aacgtgtggg caatcggccg cgaccctgga ctgtgggacg cgccggagga gttccggccg   1260
gagcggttcg tcgagagcaa gatcgacgtg aggggccatg acttccagct gctgccgttc   1320
ggctctggcc ggcgaatgtg ccccgggatc aacctcgcgc taaaggtgat ggctttgagt   1380
cttgccaatc tgctacacgg cttcgagtgg aggcttccgg acggcgtgac ggcagaggag   1440
ctgagccatg gatgaggcct tcaagctcgc ggtaccgcgt aaattcccgc tcatggtcgt   1500
ggccgagccc aggttgccag ctcgcctgta tactggcgct tgatgccagt acgtgtcttc   1560
ggttgttggc atgcgtggag tatagcacat gattttcagc tcttggaact ttgtttttaat  1620
aaaacacaaa tatatgtgtt atgttggtta tgatgaatgtg aatataaagt tgacaaccta   1680
ggtaattcga acccctattg gtatataatt ttactttatt tttgcataac tgtgtaaact   1740
ggtggtcatg gacgttgaag ttaatatttg gactgtggat tagattaaaa aaaaaaaaaa   1800
aaaaaa                                                              1806
```

<210> SEQ ID NO 4
<211> LENGTH: 513
<212> TYPE: PRT
<213> ORGANISM: Zea mays

<400> SEQUENCE: 4

```
His Glu Ala Ala Phe Leu Gly Ile Ala Leu Cys Ala Ala Ala Leu
  1               5                  10                  15

Phe Leu Leu Arg Gly Arg Arg Pro Val Tyr Asn Pro Pro Gly Pro
             20                  25                  30

Lys Pro Trp Pro Ile Ile Gly Asn Leu Asn Leu Met Gly Glu Leu Pro
         35                  40                  45

His Arg Ser Met Asn Glu Leu Ser Lys Arg Tyr Gly Pro Leu Met Gln
     50                  55                  60

Leu Trp Phe Gly Ser Leu Pro Val Val Gly Ala Ser Ala Glu Met
 65                  70                  75                  80

Ala Lys Leu Phe Leu Lys Thr Asn Asp Ala Ala Phe Ser Asp Arg Pro
                 85                  90                  95

Arg Phe Ala Val Gly Lys Tyr Thr Ala Tyr Asp Cys Ser Gly Leu Leu
            100                 105                 110

Trp Ala Pro Phe Glu Pro Tyr Leu Arg Gln Ala Arg Arg Ile Cys Ala
        115                 120                 125

Thr Glu Leu Phe Ser Ala Thr Arg Leu Glu Ser Phe Glu His Ile Arg
    130                 135                 140

Asp Glu Glu Val Arg Val Met Leu Arg Gln Leu Arg Gln Ala Ala Gly
145                 150                 155                 160

Arg Thr Val Arg Leu Arg Asp Tyr Leu Gln Met Leu Ala Leu Gly Val
```

-continued

```
            165                 170                 175
Ile Ser Arg Ile Val Leu Gly Lys Lys Tyr Val Met Glu Glu Ala Ala
                180                 185                 190
Asp Gly Glu Gly Asp Ser Ala Pro Ala Ile Thr Pro Ala Glu Phe Arg
        195                 200                 205
Glu Met Val Asp Glu Phe Phe Ala Leu His Gly Ala Phe Asn Ile Gly
    210                 215                 220
Asp Tyr Ile Pro Trp Leu Asp Trp Leu Asp Leu Gln Gly Tyr Val Ala
225                 230                 235                 240
Arg Met Lys Arg Met Lys Ala Arg Phe Gly Arg Phe Leu Glu Arg Val
                245                 250                 255
Leu Asp Val His Asn Glu Arg Arg Leu Arg Glu Gly Gly Asn Phe Val
                260                 265                 270
Ala Lys Asp Met Leu Asp Val Leu Leu Gln Leu Ala Asp Asp Thr Ser
                275                 280                 285
Leu Glu Val Gln Leu Ser Arg Asp Asn Val Lys Ala Ile Thr Gln Asp
    290                 295                 300
Leu Ile Ile Ala Gly Thr Asp Ser Asn Ala Asn Thr Leu Glu Trp Ala
305                 310                 315                 320
Val Ser Glu Leu Leu Lys Asn Pro Lys Ile Leu Ala Lys Ala Met Glu
                325                 330                 335
Glu Leu Asn His Val Ile Arg Pro Asp Arg Leu Val Thr Glu Ser Asp
                340                 345                 350
Leu Pro Arg Leu Pro Tyr Ile Glu Ala Val Leu Lys Glu Thr Met Arg
            355                 360                 365
Val His Pro Ala Ala Pro Met Leu Ala Pro His Val Ala Arg Glu Asp
    370                 375                 380
Thr Ser Val Asp Gly Tyr Asp Val Leu Ala Gly Thr Val Leu Phe Ile
385                 390                 395                 400
Asn Val Trp Ala Ile Gly Arg Asp Pro Gly Leu Trp Asp Ala Pro Glu
                405                 410                 415
Glu Phe Arg Pro Glu Arg Phe Val Glu Ser Lys Ile Asp Val Arg Gly
                420                 425                 430
His Asp Phe Gln Leu Leu Pro Phe Gly Ser Gly Arg Arg Met Cys Pro
            435                 440                 445
Gly Ile Asn Leu Ala Leu Lys Val Met Ala Leu Ser Leu Ala Asn Leu
    450                 455                 460
Leu His Gly Phe Glu Trp Arg Leu Pro Asp Gly Val Thr Ala Glu Glu
465                 470                 475                 480
Leu Ser Met Asp Glu Ala Phe Lys Leu Ala Val Pro Arg Lys Phe Pro
                485                 490                 495
Leu Met Val Val Ala Glu Pro Arg Leu Pro Ala Arg Leu Tyr Thr Gly
                500                 505                 510
Ala
```

CYTOCHROME P450 ENZYMES AND RELATED COMPOUNDS AND METHODS

This application claims priority to U.S. Provisional Patent Application Ser. No. 60/092,596, filed Jul. 12, 1998.

BACKGROUND OF THE INVENTION

Plant cytochrome P450s are now known to be involved in the metabolism and detoxification of numerous pesticides. Much of the evidence has been gathered via traditional chemistry techniques (Shuler, 15 *Crit Rev Plant Sci* 235 (1996); Bolwell et al., 37 *Phytochemistry* 1491(1994) and Frear et al., 8 *Phytochemistry* 2157 (1969)), or through use of mammalian or bacterial genes in plants (Shiota et al., 106 *Plant Physiol* 17 (1994) and O'Keefe et al., 105 *Plant Physiol* 473 (1994)).

Recently, however, endogenous plant P450s have been cloned and expressed using molecular biology techniques. For example, CYP73A1, a cytochrome isolated from Jerusalem artichoke was recently shown to metabolize chlortoluron (Pierrel, 224 *Eur J Biochem* 835 (1994). Likewise, several soybean P450s were cloned and one was shown to metabolize linuron and chlortoluron (Presentation, *Weed Sci Soc of Amer (February* 1997)).

The most up-to-date source of information on plant P450s is on the internet. As of Jul. 12, 1998, most of the information related to the CYP72A subfamily of P450s on that web site pertained to the Catharanthus (rosens) P450s, although Nicotiana and Arabidopsis P450s were also characterized. The site implied the existence of two CYP72 P450s from *Zea mays,* although the sequence information was not disclosed for either. The two were assigned separate identifiers by the web site developer. Specifically, the web site stated:

CYP72A *Zea mays*
  no accession number (318 amino acids)
  Mike Persons and Mary Schuler
  PCR 4 formerly CYp95A1 (missnamed due to a frame shift in the PCR fragment)
CPY72A1 *Zea mays* (maize)
  no accession number
  Mike Barrett
  clone A8 most like PCR fragment PCR4 from Mike Persans and Mary Schuler. The PCR4 fragment was missnamed as CYP95A1 due to a frame shift error in the sequence in the I helix region, also like Arabidopsis GSS BAC end fragment B24203 (67? identical) submitted to nomenclature committee.

The above can be found at http://drnelson.utmem.edu/biblioD.html#72A.

The concept of a multiple pesticide metabolizing P450 in corn was first proposed during the Ph.D. Dissertation of Laura Boldt on Apr. 15, 1992. FIG. 12 in the present disclosure is the table from her thesis, which indicates that corn line GA209 is not only sensitive to bentazon, but also to the herbicides imazethapyr, nicosulfuron and primisulfuron. In further research by Roger Baerg, it was shown that the in-vitro metabolism of the herbicides nicosulfuron, chlorimuron, bentazon, imazethapyr, and the insecticide malathion are all inhibited by the insecticide terbufossulfone (FIG. 13—from Baerg et al., 55 Pesticide Biochemistry and Physiology 10 (1996), initially disclosed Nov. 4, 1994 in dissertation form).

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

It is therefore an object of the present invention to provide compounds useful to protect plants from the otherwise detrimental effects of a broad spectrum of pesticides, including negative effects of herbicides and/or insecticides.

It is a further object to provide assays for discovery of new pesticide safeners, including herbicide and/or insecticide safeners.

It is yet another object to provide assays for discovery of new pesticides, including herbicide and/or insecticide assays.

It is yet another object to provide tools for pesticide metabolite analysis, including herbicide and/or insecticide metabolite analysis.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis. In this application, the term "pesticide" is used as a generic word for both herbicides and insecticides.

BRIEF DESCRIPTION OF THE DRAWINGS

FIG. 1 is the DNA (SEQ ID NO 1) and deduced amino acid sequence (SEQ ID NO 2) of CYP72A1.

FIG. 2 is the DNA (SEQ ID NO 3) and deduced amino acid sequence of CYP92A1 (SEQ ID NO 4); FIG. 4 shows comparisons of nucleotide and protein identity of CYP72A1 and CYP92A1 with known sequences. It also shows protein similarity of CYP72A1 and CYP92A1 with known sequences; FIG. 8 shows chromatographs of the production of the bentazon metabolites, in comparison to appropriate control treatments; and FIG. 9 shows chromatographs of the production of the chlortoluron metabolites, in comparison to appropriate control treatments; and FIG. 10 shows chromatographs of the production of the malathion metabolites, in comparison to appropriate control treatments; and FIG. 11 shows chromatographs of the production of the chlorimuron metabolites, in comparison to appropriate control treatments.

DETAILED DESCRIPTION OF THE INVENTION

Figure 3:
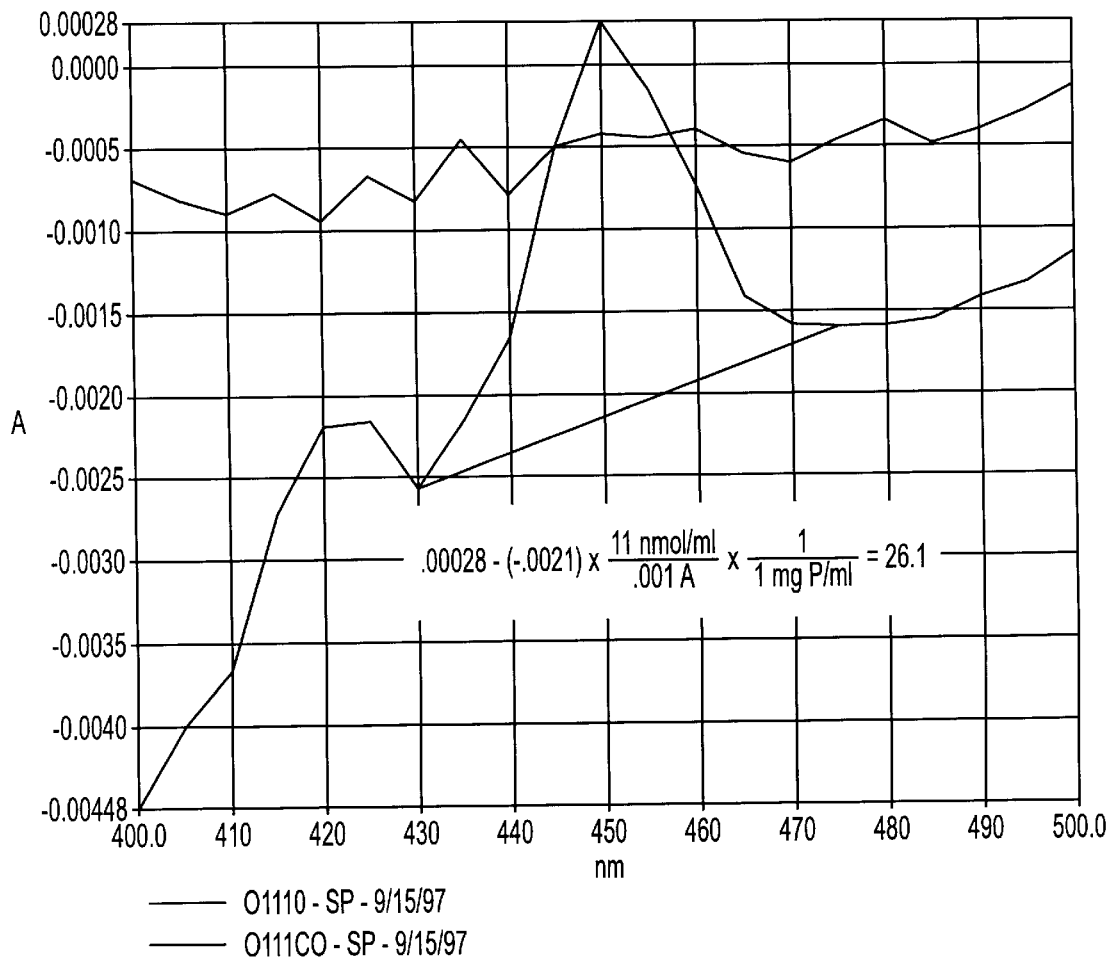
FIG. 3 is a spectra demonstrating expression of 72A1 in yeast microsomes.

The present invention provides, inter alia, nucleic acids which encode P450s in corn that, when expressed in the presence of a reductase, metabolize compounds exemplary of several distinct classes of insecticides and herbicides. The CYP72A1 P450 has been shown to metabolize the herbicides bentazon (tradename Basagran), chlorimuron (tradename Classic and others), and chlortoluron (used in Europe), and the insecticide malathion (marketed under many tradenames). Representative chromatographs showing the production of the metabolites, in comparison to appropriate control treatments, are shown in FIGS. 8–11.

The above pesticides are representative of unclassified heterocyclic herbicides (bentazon), sulfonylurea herbicides (chlorimuron), substituted urea herbicides (chlortoluron), and organophosphate insecticides (malathion). The CYP72A1 P450 thus displays a broad substrate range. Based on genetic and biochemical data gathered prior to the cloning and expression of the CYP72A1 P450, additional substrates in the sulfonylurea family of herbicides (particularly nicosulfuron, primisulfuron, prosulfuron, and rimsulfuron), the herbicide imazethapyr (tradename Pursuit and others, from the imidazolinone family of herbicides), the herbicide fumetsulam (tradename Broadstrike and others, from the triazolopyrimidine family of herbicides), experimental herbicides under development related to sulcantrione, and other organophosphate insecticides would be metabolized by the CYP72A1 P450. However, the CYP72A1 P450 does not metabolize all substrates which have been tested. Unmetabolized substrates include the herbicides alachlor, 2,4-D, linuron, dicamba and chlorsulfuron.

The present invention can be used in the development of herbicide resistant crops. For instance, crops transformed with SEQ ID NO 1 would be resistant to herbicides from several herbicide chemical families having different sites of action. Historically, herbicide resistant crops that have been developed are resistant to only one chemical family or inhibitors of one site of action. The present invention overcomes many of the limitations of previously developed herbicide resistant crops. In addition, the invention can be used in the discovery and development of new herbicides and other pesticides.

The gene can also be expressed in other plants, such as *Arabidopsis thaliana,* or in a heterologous system, such as yeast cells, to demonstrate and study the metabolism of candidate pesticide molecules by the CYP72A1 P450. The present invention can also be used to generate P450-produced pesticide metabolites needed for pesticide registration studies. Moreover, the present invention includes the use of the nucleic acid compounds to generate nucleic acid probes to test for the induction activity of new candidate safeners. It can also provide probes and primers for identification of additional P450s.

Therefore, the present invention includes nucleic acid compounds comprising SEQ ID NO 1. The nucleic acid which is SEQ ID NO 1 is preferred. However, portions of SEQ ID NO 1 are also provided for the use as primers and probes for molecular biology research or chemical assays.

Vectors comprising the nucleic acids, in particular, SEQ ID NO 1 are also provided. Vectors may be obtained from various commercial sources, including Clontech Laboratories, Inc. (Palo Alto, Calif.), Stratagene (La Jolla, Calif.), Invitrogen (Carlsbad, Cailf.), New England Biolabs (Beverly, Mass.) and Promega (Madison, Wis.). Preferred vectors are those which are capable of transferring the sequences disclosed herein into plant cells or plant parts.

Also provided are cells comprising the nucleic acids, in particular, SEQ ID NO 1. Preferred cells are eukaryotic cells. Most preferred are yeast (the Saccharomycetes) and plants. Any species of yeast are consider within the scope of the present invention; however, *S. cerevisiae* cells are preferred. The most preferred strains are WAT 11 and WAT 21, with WAT 11 preferred as between the two.

Included within the scope of the present invention, with particular regard to the nucleic acids above, are allelic variants, degenerate sequences and homologues. The present invention also includes variants due to laboratory manipulation, such as, but not limited to, variants produced during polymerase chain reaction amplification or site directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide. Lastly, a nucleic acid sequence homologous to the exemplified nucleic acid molecules (or allelic variants or degenerates thereof) may have at least 85%, preferably 90%, and most preferably 95% sequence identity with a nucleic acid molecule in the sequence listing.

It is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

In another embodiment of the present invention, a preferred nucleic acid molecule includes an isolated nucleic acid molecule which is at least about 50 nucleotides, or at least about 150 nucleotides, and which hybridizes under conditions which preferably allow about 50% base pair mismatch, more preferably under conditions which allow about 45% base pair mismatch, more preferably under conditions which allow about 40% base pair mismatch, more preferably under conditions which allow about 35% base pair mismatch, more preferably under conditions which allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO 1 and SEQ ID NO 3.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridized under conditions designed to allow a desired amount of base pair mismatch.

Transformation of cells with the compounds of the present invention can be accomplished according to known procedures. For example, infective, vector-containing bacterial strains (such as *Agrobacterium rhizogenes* and *Agrobacterium tumefaciens*) may be used for transformation. Zambryski, 43 *Ann. Rev. Pl. Physiol. Pl. Mol. Biol.* 465 (1992). The following procedures are also well-known: Pollen-tube transformation [Zhon-xun et al., 6 *Plant Molec. Bio.* 165 (1988)]; direct transformation of germinating seeds [Toepfer et al., 1 *Plant Cell* 133 (1989)]; polyethylene glycol or electroporation transformation [Christou et al., 84 *Proc. Nat. Acad. Sci.* 3662 (1987)]; and biolistic processes [Yang & Cristou, *Particle Bombardment Technology for Gene Transfer* (1994)]. The transformed cells are also within the scope of the present invention.

The transformed cells may be induced to form transformed plants via organogenesis or embryogenesis, according to the procedures of Dixon *Plant Cell Culture: A Practical Approach* (IRL Press, Oxford 1987).

Moreover, any plants or plant cells or parts are within the scope of the present invention. For instance, whole plants, embryos and seeds are considered part of the present invention, as well as shoots, flowers, leaves, leaf tips and the like. The most preferred plant is maize, although any of the following plants are also within the scope of the present invention: soybean, beet, tobacco, wheat, barley, poppy, rape, sunflower, alfalfa, sorghum, rose, carnation, gerbera, carrot, tomato, lettuce, chicory, pepper, melon and cabbage.

In another aspect of the present invention, there are included nucleic acid compounds comprising SEQ ID NO 3. Eukaryotes comprising a nucleic acid compound of SEQ ID NO 3 is specifically provided. Maize is the preferred eukaryote.

The present invention also provides methods to determine the ability of a test compound to protect a plant from the deleterious effects of a pesticide, comprising a first step of contacting the test compound with a eukaryote of the present invention, and a second step of determining if the eukaryote is induced to produce a nucleic acid of the present invention, in particular, SEQ ID NO 1, RNA transcribed therefrom, or SEQ ID NO 2. Those in the art realize that the second step can be accomplished by routine means, such as, but not limited to, PCR analysis, genomic southern blot analysis, or western blot analysis.

Other methods herein provided are those useful for determining the ability of a test compound to be metabolized by a eukaryote of the present invention, comprising a first step of contacting the eukaryote with the test compound and a second step of determining the existence of metabolites. As above, detection of metabolites is routine in the art. For example, the test compound can carry a physical label, usually a radioactive or fluorescent label. Typical radioactive labels are $^3H$, $^{14}C$ and $^{23}P$.

Also provided are methods to express an amino acid compound of the present invention, comprising transforming a eukaryote with a SEQ ID NO 1, and inducing SEQ ID NO 1 with napthalic acid.

In another embodiment, there are provided methods to cause pesticide resistance in a plant, comprising causing the plant to express an amino acid compound of claim 14, provided that the pesticide to which the plant is resistant is selected from the group consisting of: heterocyclic herbicides, sulfonylurea herbicides, substituted urea herbicides and organophosphate insecticides.

Lastly, the present invention includes methods to alter the naturally-occurring expression pattern of the nucleic acids provided so as to either delay or speed expression. In particular, in order to practice the altered expression pattern aspect of the present invention, one would construct a vector which provided for either an early or late promoter in conjunction with the present sequences. For instance, the following promoters would be useful in early expression of the present sequences:

Ogs4B (Tsuchiya et al., 36 *Plant Cell Physiology* 487 (1994)

TA29 (Koltunow et al., 2 *Plant Cell* 1201 (1990)

A3 & A9 (Paul et al., 19 *Plant Molecular Biology* 611 (1992)

In order to then constitutively express the sequences described above, the construct optionally contains, for example, a 35S promoter. Transformation of plants with these sequences would be according to known procedures as described above. Plants can be grown according to known procedures.

Proteins which would result from expression of the nucleic acid molecules herein disclosed are preferred, with the proteins which would result from expression of the exemplified compounds being most preferred. It is understood that proteins which would result from expression of allelic variants of the exemplified sequences, as well as proteins which would result from the expression of nucleic acid molecules which hybridize under stringent hybridization conditions to the nucleic acid molecules exemplified are within the scope of the present invention as well. Lastly, an amino acid sequence substantially homologous to a referent protein will have at least 85% sequence identity, preferably 90%, and most preferably 95% sequence homology with the amino acid sequence of a referent protein or a peptide thereof. For example, an amino acid sequence is substantially homologous to a referent P450 protein if, when aligned with a referent P450 protein, at least 85% of its amino acid residues are the same. Specifically provided are amino acid compounds comprising SEQ ID NO 2 and/or SEQ ID NO 3.

The minimal size of a protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules, The minimal size of such nucleic acid molecules is typically at least 12 to about 15 nucleotides in length if the nucleic acid molecules are GC-rich and at least about 15 to about 17 bases in length if they are AT-rich. As such, the minimal size of a nucleic acid molecule used to encode a protein homolog of the present invention is from about 12 to about 18 nucleotides and may be 25 nucleotides in length. Thus, the minimal size of a cytochrome P450 protein homolog of the present invention is from about 4 to about 6 amino acids in length. There is no limit, other than a practical limit, on the maximal size of such a nucleic acid molecule in that the nucleic acid molecule can include gene, and entire gene, multiple genes, or portions thereof. The preferred size of a protein encoded by a nucleic acid molecule of the present invention depends on whether a full-length, fusion, multivalent or functional portion of such a protein is desired. Preferably, the preferred size of a protein encoded by a nucleic acid molecule of the present invention is a portion of the protein that which is at least 30 amino acids, more preferably at least 35 amino acids and even more preferably at least 45 amino acids in length.

EXAMPLES

Example 1

Cloning, Sequencing and Estimating Copy Number of Maize P450s

A maize cDNA library was constructed from napthalic anhydride (NA)-treated Pioneer 3343IR 3.5-day-old seedlings using lambda-ZAPII vector kit (Stratagene).

The library was screened under high stringency conditions by two P450 clones generated by PCR to heme-binding region and inducible by naptalic acid. Both PCR products were labeled with [$^{32}$P]-dCTP by random priming method. Clones were separated into two subsets based on the similarity of the sequencing information. The longest clones from each subset were completely sequenced. Both clones were truncated at the 5'-end. The library was rescreened using the longer clones. One of the genes was recovered as a full length (CYP72A1), whereas the second gene (CYP92A1) was still truncated.

Northern blot analysis was performed with total RNA isolated from control and agarose gel electrophoresis and hybridized under high stringency conditions. To estimate the copy number, Southern blot analysis was performed using genomic DNA from 3343IR maize which was digested with SacI EcoRV, EcoRI, HindIII, and BamHI. The analysis was carried out under high stringency (65 degrees Celsius in 0.1×SSC and 0.1% SDS).

Example 2

Expression and Sequence Confirmation of Maize P450s in Yeast

Both genes (CYP72A1 and CYP92A1), obtained as described in Example 1, were introduced into pYeDP60 vector for yeast expression. CYP72A1 was introduced as a full length gene with in-frame Met 1 and 8 as the start codons, while CYP92A1 was modified for the expression.

Approximately 8×10$^6$ plaque-forming units were screened by two P450 fragments. 73 positive clones were isolated and sequenced. Sequence homology was used to separate these clones into two groups. Secondary screening using the cDNA inserts from the longest clones identified an additional 56 clones which were sequenced at the ends. All the sequences represented one of the two genes. CYP 72A1 was isolated presumably as a full-length gene, however, CYP92A1 was still missing 30–50 bases at the amino terminus after rescreening. These genes and their deduced amino acid sequences showed homology to several plant P450s. See FIG. 4.

Example 3

Figure 5:
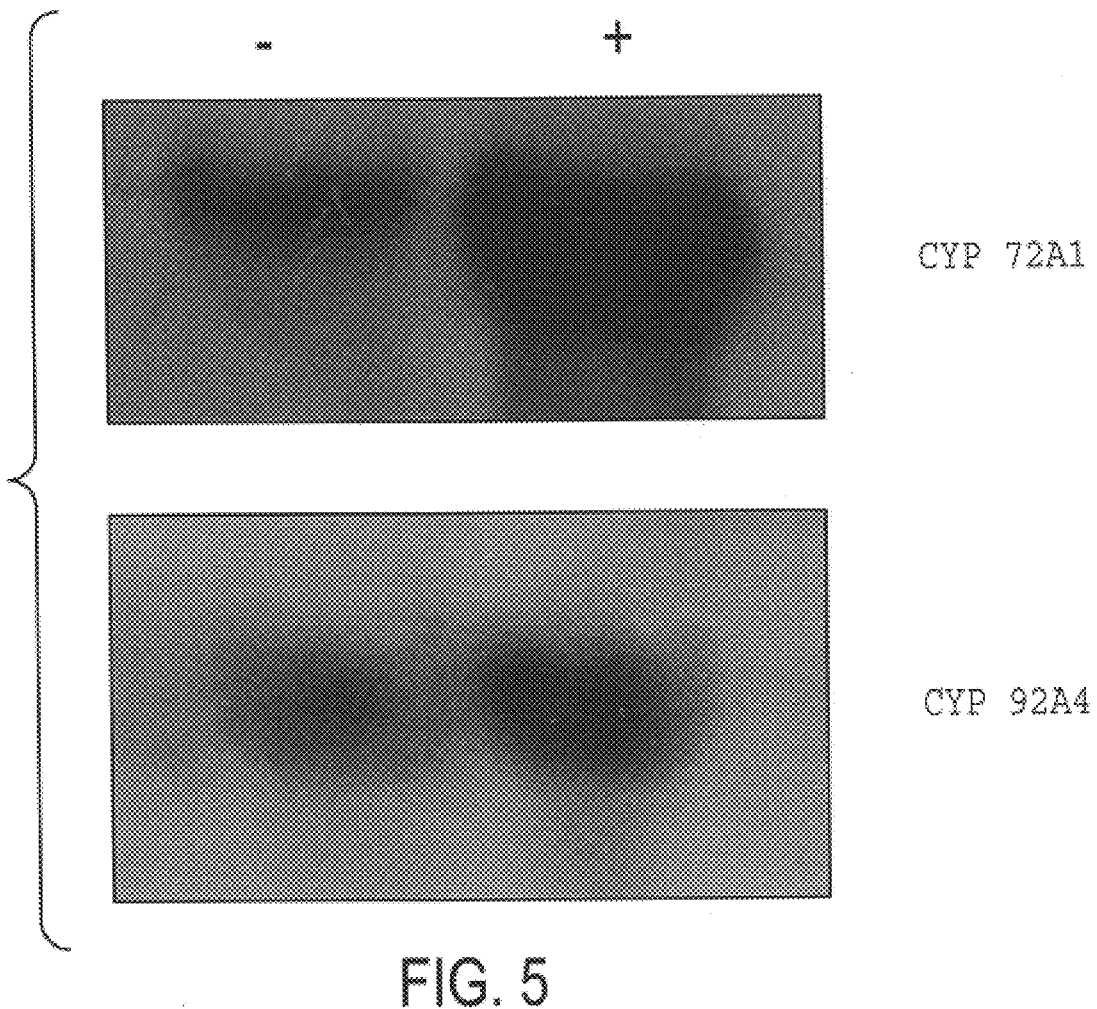
FIG. 5 is a genomic blot showing induction of expression of CY72A1 and CYP92A1 by NA-treatment.
Figure 6:
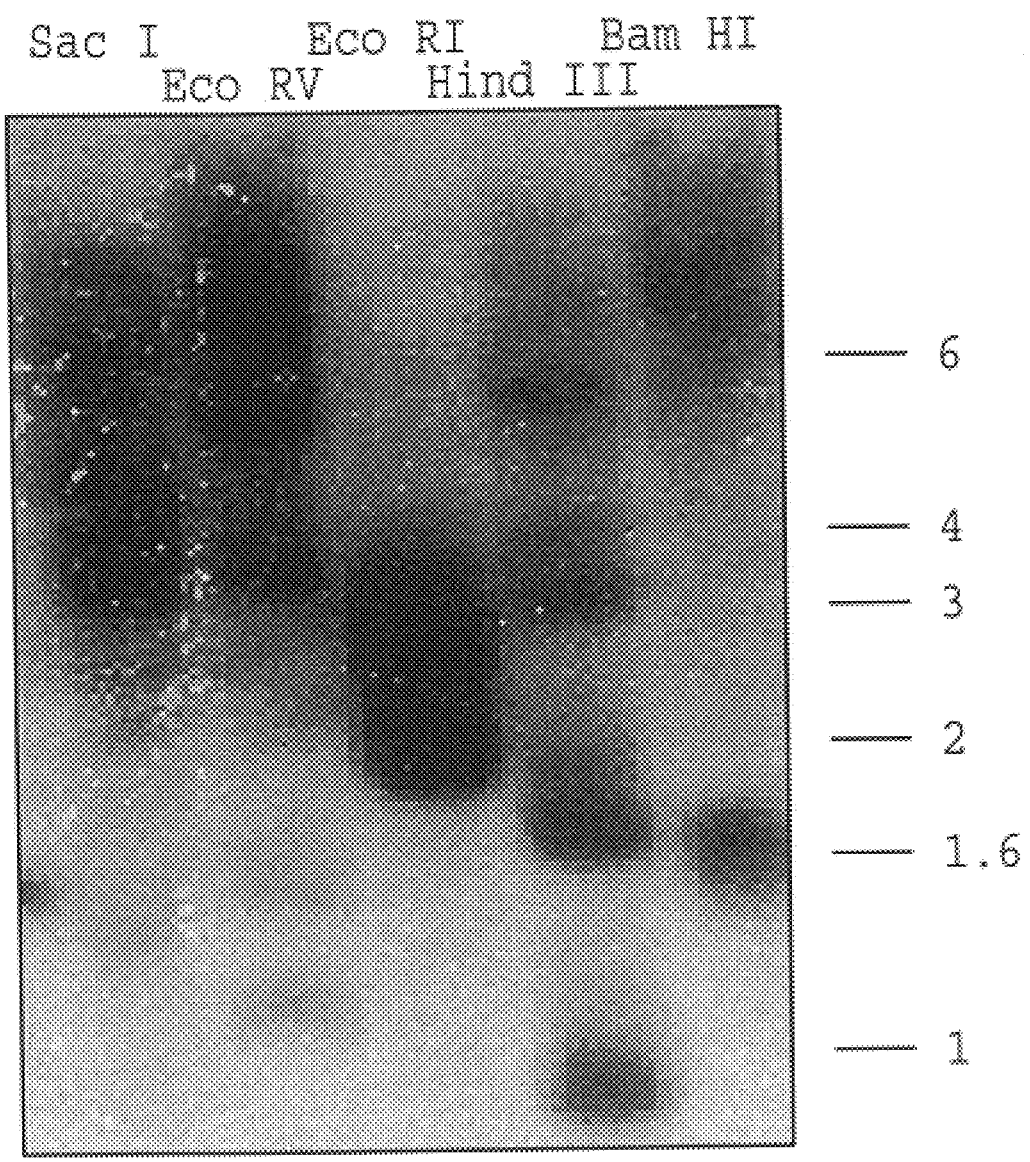
FIG. 6 is the hybridization pattern of CYP72A1.
Figure 7:
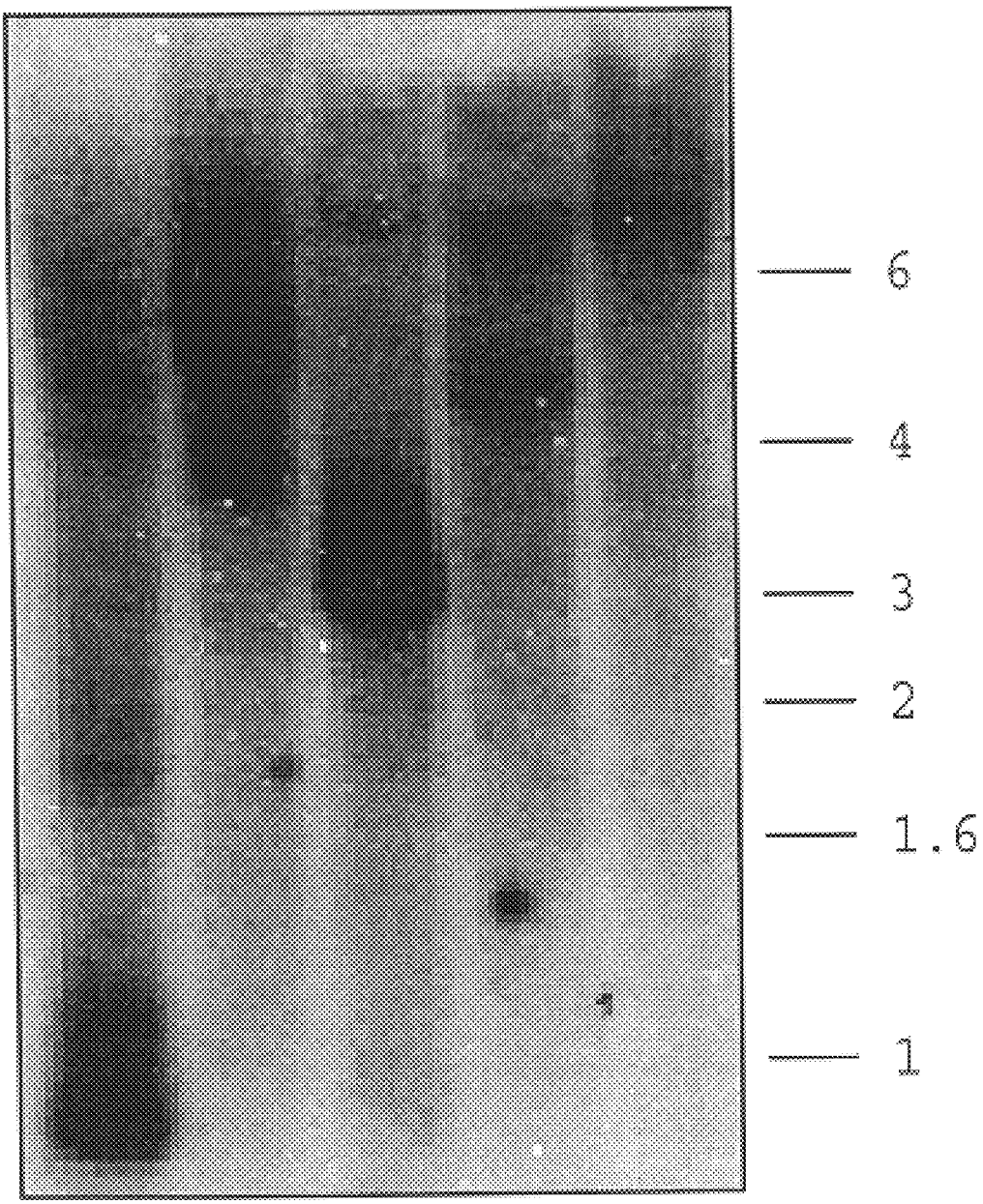
FIG. 7 is the hybridization pattern of CYP92A1.

Induction of CYP72A1 and CYP92A1 by Napthalic Acid and Confirmation of Copy Number The expression of both genes (CYP72A1 and CYP92A1) was induced by NA-treatment, but to different extents: CYP72A1 was highly induced, whereas CYP92A1 was induced significantly less (FIG. 5). Based on the results of the genomic Southern blot analysis, the hybridization patterns were consistent with those predicted from the restriction patterns of the corresponding cDNAs. Distinct patterns indicated that individual probes did not cross-hybridize to other P450 genes ad showed that CYP72A1 is likely to be present as two copies in the genome of 3343IR maize, and CYP92A1 as a single copy (FIGS. 6 & 7). Certain physicochemical characteristics for the deduced proteins, antigenicity and secondary structure were calculated using Network Protein Sequence Analysis at IBCP, France.

Example 4

Optional Strategies for Cloning and Expressing CYP72A1 and CYP92A1

Prepare RNA from NA-induced maize shoots. One or more of the following techniques can then be used: primers can be designed from the flanking heme region according to Ohbayashi et al, 1993. Alternatively, degenerate 5' primers to heme region may be uses, with 3' primer to the poly A tail, according to Meijer et al., 1993). Another acceptable method is to use nested PCR, with the first round using 5' primer to region upstream from heme region, according to Frey et al., 1995.

Clone selection criteria can include identification of induction of message with NA, identification of RFLP co-segregation with phenotypes in repulsion phase homozygotes and/or differential expression between GA209 and ie. B73 (wild type).

Expression strategies include using both full length or truncated (Met 8 start site) CYP72A1 cDNA in yeast strains WAT11, WAT21 W (R) from Philippe Urban and Denis Pompon, with, optionally, yeast vector pYeDP60. Expression is ideally achieved with full length cDNA and WAT11. Expression may also require 36 hours rather than 24 hours of galactose induction prior to microsome preparation. Glucose (SGI) or galactose (SLI) media prior to induction will give expression.

Metabolism experiments can be accomplished using microsomes prepared from yeast cells. The substrates can be incubated with [$^{14}$C]-labeled substrates and products analyzed by HPLC.

Although the present invention has been fully described herein, it is to be noted that various changes and modifications are apparent to those skilled in the art. Such changes and modifications are to be understood as included within the scope of the present invention as defined by the appended claims.

What is claimed is:

1. An isolated nucleic acid molecule, wherein said nucleic acid molecule comprises a nucleic acid sequence selected from the group consisting of:

(a) a nucleic acid sequence which has at least 95% identity to SEQ ID NO:1, wherein said identity can be determined using the DNAsis computer program and default parameters; and (b) a nucleic acid sequence which has at least 95% identity to SEQ ID NO:3, wherein said identity can be determined using the DNAsis computer program and default parameters; wherein the nucleic acid sequences of (a) and (b) each encodes an amino acid having cytochrome P450 activity.

2. A vector comprising a nucleic acid molecule of claim 1.

3. A cell transformed with a nucleic acid molecule of claim 1.

4. A eukaryote transformed with a nucleic acid molecule of claim 1.

5. A eukaryote of claim 4, which is yeast.

6. A eukaryote of claim 4, which is a plant.

7. A eukaryote of claim 6, which is maize.

8. A eukaryote of claim 4, which is selected from the group consisting of: soybean, beet, tobacco, wheat, barley, poppy, rape, sunflower, alfalfa, sorghum, rose, carnation, gerbera, carrot, tomato, lettuce, chicory, pepper, melon and cabbage.

9. A plant transformed with a nucleic acid molecule of claim 1.

10. A plant part of claim 9, which is a seed.

11. A nucleic acid molecule selected from the group consisting of SEQ ID NO 1, and SEQ ID NO 3.

12. An isolated nucleic acid molecule, wherein said nucleic acid molecule comprises a nucleic acid sequence comprising at least 50 contiguous nucleotides of the sequence selected from the group consisting of SEQ ID NO 1, and SEQ ID NO 3.

13. A method to express an amino acid sequence selected from the group consisting of SEQ ID NO 2, comprising transforming a eukaryote with a SEQ ID NO 1, and inducing SEQ ID NO 1 with napthalic acid.

14. A method to cause pesticide resistance in a plant, comprising causing the plant to express an amino acid sequence selected from the group consisting of SEQ ID NO 2, and SEQ ID NO 4, provided that the pesticide to which the plant is resistant is selected from the group consisting of: heterocyclic herbicides, sulfonylurea herbicides, substituted urea herbicides and organophosphate insecticides.

* * * * *